United States Patent [19]
Nakanishi

[11] 3,948,919
[45] Apr. 6, 1976

[54] 2-HYDROXYMETHYL-3-HYDROXY-6-(1-HYDROXY-2-T-BUTYLAMINOETHYL)-PYRIDINE PREPARATION AND INTERMEDIATE COMPOUNDS

[75] Inventor: Susumu Nakanishi, East Lyme, Conn.

[73] Assignee: Pfizer Inc., New York, N.Y.

[22] Filed: Oct. 9, 1974

[21] Appl. No.: 513,213

Related U.S. Application Data

[63] Continuation-in-part of Ser. No. 428,451, Dec. 26, 1973, abandoned.

[52] U.S. Cl............. 260/296 R; 424/263; 260/297 B
[51] Int. Cl.².................................. C07D 213/69
[58] Field of Search......... 260/297 B, 297 R, 570.6, 260/296 R, 340.3

[56] References Cited
UNITED STATES PATENTS

| | | | |
|---|---|---|---|
| 3,253,034 | 5/1966 | McLoughlin..................... | 260/570.6 |
| 3,341,594 | 9/1967 | Thoma, et al..................... | 260/570.6 |
| 3,700,681 | 10/1972 | Barth............................. | 260/296 AE |

FOREIGN PATENTS OR APPLICATIONS

| | | | |
|---|---|---|---|
| 643,778 | 2/1964 | Belgium........................... | 260/340.3 |
| 643,779 | 2/1964 | Belgium........................... | 260/340.3 |

OTHER PUBLICATIONS

Chem. Abstracts, 77:5492m, (1972); Abstract of Japanese Patent 72 03,832, 02021972, Nakanishi et al.

*Primary Examiner*—John D. Randolph
*Attorney, Agent, or Firm*—Connolly and Hutz

[57] ABSTRACT

Process for preparing 2-hydroxymethyl-3-hydroxy-6-(1-hydroxy-2-t-butylaminoethyl)pyridine and the acid addition salts thereof which are useful as β-adrenergic agonist bronchodilators in mammals, and the intermediate compounds 2-hydroxymethyl-3-benzyloxypyridine-6-epoxyethane, 2-phenyl-4H-pyrido[3,2-d]-1,3-dioxin-6-epoxyethane and 2,2-disubstituted-4H-pyrido[3,2-d]-1,3-dioxin-6-epoxyethanes.

13 Claims, No Drawings

2-HYDROXYMETHYL-3-HYDROXY-6-(1-HYDROXY-2-T-BUTYLAMINOETHYL)PYRIDINE PREPARATION AND INTERMEDIATE COMPOUNDS

CROSS-REFERENCE TO RELATED APPLICATIONS

This application is a continuation-in-part of copending application Ser. No. 428,451, filed Dec. 26, 1973, now abandoned.

BACKGROUND OF THE INVENTION

U.S. Pat. No. 3,700,681 issued on Oct. 24, 1972 discloses and claims bronchodilators for use in mammals identified as 2-hydroxymethyl-3-hydroxy-6-(1-hydroxy-2-aminoethyl)pyridines. Included in this group of pyridines disclosed and claimed in U.S. Pat. No. 3,700,681 is the t-butyl form of the above-identified pyridines which is represented by the following formula:

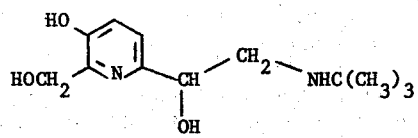

The present invention relates to a process not disclosed or suggested in U.S. Pat. No. 3,700,681 for producing the t-butyl form of the subject pyridines. The present process has particular interest since it was unexpectedly found the t-butyl form of the patented pyridines can be produced with a two-step reaction sequence as opposed to the many reaction steps required in U.S. Pat. No. 3,700,681. In addition, it was determined that the present process unexpectedly produces the product in high yield and purity.

Also within the purview of the instant invention are the compounds 2-hydroxymethyl-3-benzyloxypyridine-6-epoxyethane, 2-phenyl-4H-pyrido[3,2-d]-1,3-dioxin-6-epoxyethane and 2,2-disubstituted-4H-pyrido[3,2-d]-1,3-dioxin-6-epoxyethanes. These compounds were found to be excellent intermediates in the process of the present invention.

SUMMARY OF THE INVENTION

The process of the present invention relates to three related sequences of reaction steps wherein each sequence produces the desired form of the compound of the present invention. The first sequence of reaction steps involves heating 2-hydroxymethyl-3-benzyloxypyridine-6-epoxyethane with at least a molar amount of t-butylamine after which the resulting product is hydrogenated in the presence of a palladium catalyst to produce 2-hydroxymethyl-3-hydroxy-6-(1-hydroxy-2-t-butylaminoethyl)pyridine or its acid addition salts. This synthesis is illustrated by the following series of reactions:

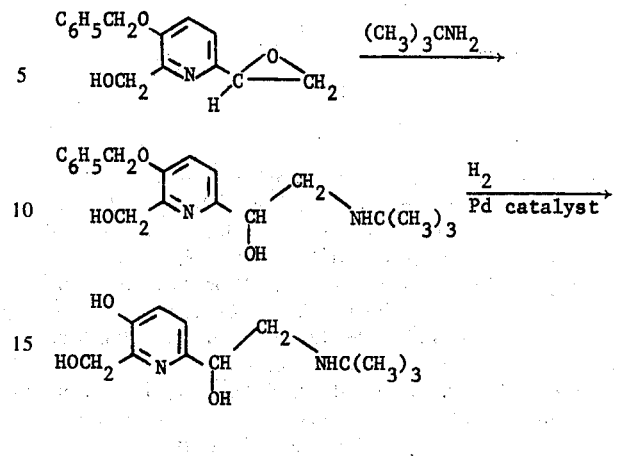

As to the second sequence of reaction steps to produce the same t-butyl form, 2-phenyl-4H-pyrido[3,2-d]-1,3-dioxin-6-epoxyethane is heated with at least a molar amount of t-butylamine after which the resulting product is acid hydrolyzed at a pH of from about 1 to 6 to produce the product of the present invention. This sequence is illustrated as follows:

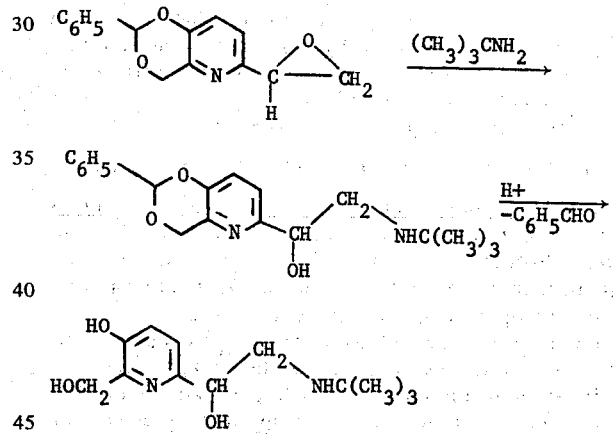

The third sequence of reaction steps to produce the same t-butyl form, a 2,2-disubstituted-4H-pyrido[3,2-d]-1,3-dioxin-6-epoxyethane is heated with at least a molar amount of t-butylamine after which the resulting product is acid hydrolyzed at a pH of from about 1 to 6 to produce the product of the present invention. This sequence is illustrated as follows:

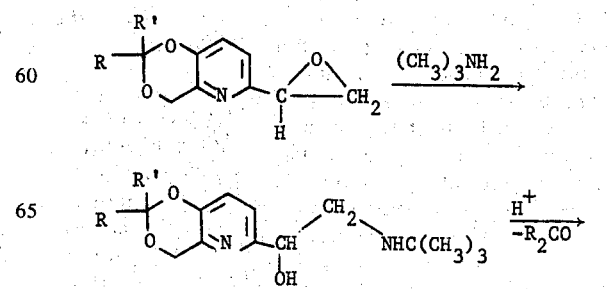

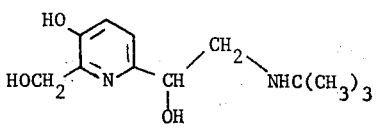

wherein R and R' are each phenyl or methyl.

Included in the present invention is the process for producing the mono- and diacid addition salts of the t-butyl form of the compounds of the present invention which are highly acceptable as bronchodilators in mammals. These can be formed, inter alia, by adding the desired acid such as HCl to the product of the first step of the first reaction sequence illustrated above or by adding HCl to the product of the second reaction sequence illustrated above. Additional suitable acids which can be used are identified hereinafter.

Finally, the present invention encompasses as intermediate compounds used in the above illustrated reaction sequences 2-hydroxymethyl-3-benzyloxypyridine-6-epoxyethane, 2-phenyl-4H-pyrido[3,2-d]-1,3-dioxin-6-epoxyethane and 2,2-disubstituted-4H-pyrido[3,2-d]-1,3-dioxin-6-epoxyethane, in particular 2,2-dimethyl-4H-pyrido[3,2-d]-1,3-dioxin-6-epoxyethane. The preparation of these compounds is described in the hereinafter illustrative Examples.

A fourth sequence within the scope of the present invention utilizes the opening of the epoxide with a hydrogen halide followed by treatment of the resulting halohydrin with t-butyl amine to yield the intermediate amino alcohol which is subsequently deblocked using the appropriate techniques described herein.

DETAILED DESCRIPTION OF THE INVENTION

In carrying out the above illustrated reaction sequences, it is pointed out that in the catalytic hydrogenation step illustrated heretofore in the first reaction sequence, pressure conditions can vary from atmospheric pressure up to about 60 psi gauge at ambient room temperature. The conditions are not critical and are to be selected according to the reaction rate desired.

In order to minimize the hydrogenolysis of the hydroxyl group on the basic side chain it is preferred that water be present during the hydrogenation reaction. The amount of water can vary from a trace amount to as much as 30 equivalent moles, the limiting factor being the dilution effect of the added water on the rate of the debenzylation reaction. The preferred amount of water in this reaction is from 10 to 20 equivalent moles.

The palladium catalyst can be used by itself; however, the preferred form is a palladium on charcoal and preferably 5% palladium on charcoal. In addition, palladium on barium sulphate can also be used as catalyst in the present invention. Also found to be suitable are palladium black which is plain red palladium and palladium oxide which is reduced to palladium under the conditions of hydrogenation. Raney nickel may also be useful in the process as a catalyst.

The heating or temperature conditions used in the first step of both of the reaction sequences with the t-butylamine are not overly critical and depend entirely on the desired rate of reaction. Temperatures of 35° C. up to reflux temperature are preferred in an open reaction system. However, if the reaction sequence is carried out in a closed system, reflux temperatures up to 85° C. are preferred. At a temperature of 75° C. in a closed vessel, reaction times of the order of one to five hours are generally required.

During the acid hydrolysis step in the second and third reaction sequences illustrated heretofore, the product of the previous step is hydrolyzed at a pH of from about 1 to 6, preferably 2 to 4. The hydrolysis is carried out in conventional manner and all mineral acids conventionally used for acid hydrolysis are suitable. The preferred acids are hydrochloric, sulfuric, phosphoric and nitric because of their ready availability.

It is, of course, part of this invention that the hydrochloride or other acid addition salt of the mono- or diacid type can be prepared. This can be achieved, inter alia, by adding a suitable acid such as hydrochloric acid to the product of the first step of the first reaction sequence illustrated heretofore or by adding hydrochloric acid to the product of the second reaction step of the second reaction sequence illustrated heretofore. Examples of other acids which provide pharmaceutically acceptable anions are hydrobromic, hydroiodic, nitric, sulfonic, sulfurous, phosphonic, acetic, lactic, citric, tartaric, succinic, maleic, and gluconic acids. If it is desired to produce the free base after the acid salt compound has been produced, the acid salt can be neutralized by reacting the compound with a base material such as sodium hydroxide. Thereafter the free base can be converted to any other desired acid addition salt. It should be noted that the diacid addition salt is the preferred form of these t-butyl pyridine compounds.

The phenyl moieties may include non-reacting, interfering or blocking substituents. It will be appreciated by those skilled in the art that the 3-benzyloxy substituent of the starting material for the first reaction sequence and the 2-phenyl substituent of the starting material for the second and third reaction sequences may be substituted with any desired non-reacting interfering substituent. A preferred blocking group within this context is p-nitrobenzyloxy for the first reaction scheme and p-nitrophenyl for the second and third schemes.

EXAMPLE 1

2-Hydroxymethyl-3-hydroxy-6-(1-hydroxy-2-t-butylaminoethyl)pyridine dihydrochloride A. 2-Hydroxymethyl-3-benzyloxypyridine-6-epoxyethane.

A solution of 700 g. (2.88 moles) of 2-hydroxymethyl-3-benzyloxypyridine-6-carboxaldehyde (U.S. Pat. No. 3,700,681) in 6.5 l. of dry tetrahydrofuran is stirred under a nitrogen atmosphere at 15° ± 2° C. while 381 ml. (3.02 moles) of trimethylchlorosylane is added over a 5 min. period. Stirring is continued for an additional 15 min., followed by the addition of 417 ml. of triethylamine. The reaction mixture is warmed to 25° C., and the trimethylamine hydrochloride salt filtered.

The resulting filtrate is then added dropwise to a suspension of sodium hydride (128 g. of 57% sodium hydride in oil suspension washed with dry tetrahydrofuran; 3.16 moles) in 4.67 l. of dry dimethylsulfoxide cooled to 0°–5° C. Following the addition, which requires 20 min., 676 g. (3.31 moles) of powdered trimethylsulfonium iodide is added; and the mixture allowed to warm to room temperature.

Water (108 ml.) is added dropwise over a 1 hr. period to decompose excess hydride, and the mixture allowed to stir for an additional hour. The mixture is then added to 43 l. of ice-water and extracted several times with isopropyl ether. The combined extracts are washed with an aqueous saturated sodium chloride solution and dried over anhydrous sodium sulfate. Removal of the solvent under reduced pressure provides the intermediate product as an oil, 575 g. (78% yield).

NMR assay (CDCl$_3$): peaks — ppm ($\delta$): 3.0 (2H of epoxide); 3.9 (1H of epoxide); 4.3 (1H of OH); 4.8 (2H of CH$_2$OH); 5.0 (2H of benzyl); 7.05 (2H — C$_4$, C$_5$ or pyridine) and 7.3 (5H of phenyl).

B.  2-Hydroxymethyl-3-benzyloxy-6-(1-hydroxy-2-t-butylaminoethyl)pyridine dihydrochloride To 3.6 l. of t-butylamine is added 7.32 g. (0.0285 mole) of 2-hydroxymethyl-3-benzyloxypyridine-6-epoxyethane, and the resulting mixture heated under reflux at atmospheric pressure for 47 hrs. The reaction mixture is evaporated to an oil, which is treated with 1 l. of tetrahydrofuran and concentrated under reduced pressure to dryness. The residual oil is again dissolved in tetrahydrofuran (4.32 l.) and is subsequently treated with 592 ml. of 12N hydrochloric acid (7.1 moles) with stirring over a 1-hour period. The volume is reduced by concentration to approximately one-half and the crystallized 2-hydroxymethyl-3-benzyloxy-6-(1-hydroxy-2-t-butylaminoethyl)pyridine dihydrochloride is filtered and dried in vacuo, 1.1 kg. (68% yield), m.p. 186°–189° C.

C.  2-Hydroxymethyl-3-hydroxy-6-(1-hydroxy-2-t-butylaminoethyl)pyridine dihydrochloride To 5.5 l. of absolute methanol is added 675 g. (1.67 moles) of the above benzyloxy compound, 199 ml. of distilled water and 347.4 g. of wet 5% palladium-on-charcoal (50% catalyst; 50% water), and the mixture stirred in a 2 gal. hydrogenation autoclave at room temperature and at a hydrogen pressure of 50 p.s.i. After 3 hrs. and 45 min., the uptake of hydrogen ceases, and the spent catalyst is filtered from the hydrogenation mixture. The filtrate is concentrated in vacuo to an oil which is dissolved in 3 l. of absolute ethanol. The water is azeotroped by concentrating to an oil, which is then dissolved in 1 l. of methanol containing 47 ml. of ethanolic hydrogen chloride. After stirring the solution for 30 min., 4 l. of isopropyl ether is added and the resulting precipitate allowed to stir at room temperature overnight. The product is filtered, washed with isopropyl ether and dried in vacuo, 509 g. (97.5% yield). Further purification of the final product is effected by recrystallization from methanol-acetone, 470 g., m.p. 185°–187° C., dec.

The product is identical with that reported in U.S. Pat. No. 3,700,681.

EXAMPLE 2

2-Hydroxymethyl-3-hydroxy-6-(1-hydroxy-2-t-butylaminoethyl)pyridine dihydrochloride A.  6-Hydroxymethyl-2-phenyl-4H-pyrido[3,2-d]-1,3-dioxin.

To a stirred suspension of 31 g. (0.2 mole) of 2,6-bis-(hydroxymethyl)-3-hydroxypyridine (U.S. Pat. No. 3,700,681) in 101 ml. (1 mole) of benzaldehyde at 20°–25° C. is added dropwise over 45 min. 56.7 g. (0.4 mole) of borontrifluoride etherate. The mixture is allowed to stir at room temperature for 2 hrs., and the excess benzaldehyde removed under reduced pressure. The residue, after standing at room temperature, is added to 75 ml. of a 10M aqueous sodium hydroxide solution, and the product extracted into methylene dichloride. The organic phase is separated, concentrated in vacuo to 100 ml. and the methylene dichloride diluted with n-hexane. The crude product which crystallizes is filtered and dried, 37.4 g. (77% yield), m.p. 85°–89° C. Further purification is effected by recrystallization from acetone-n-hexane, 22.1 g., m.p. 114°–118° C.

Anal. Calc'd for C$_{14}$H$_{13}$O$_3$N: C, 69.13; H, 5.39; N, 5.76. Found: C, 69.21; H, 5.43; N, 5.70.

B.  6-Formyl-2-phenyl-4H-pyrido[3,2-d]-1,3-dioxin.

To a suspension of 38.8 g. (0.4 mole) of activated manganese dioxide in 400 ml. of benzene is added 48.6 g. (0.2 mole) of 6-hydroxymethyl-2-phenyl-4H-pyrido[3,2-d]-1,3-dioxin in 250 ml. of the same solvent, and the mixture stirred at the reflux temperature overnight. The mixture is filtered while hot (50° C.) and the filtrate concentrated under vacuum to an oily foam, 49.7 g. The intermediate product is purified by chromatographing on a silica gel column (1 kg. 60–200 mesh silica gel; 8 cm × 75 cm column), the product being eluted with ethyl acetate. The eluates are combined and evaporated to dryness, 11,75 g., m.p. 110°–114° C.

Anal. Calc'd for C$_{14}$H$_{11}$O$_3$N: C, 69.71; H, 4.60; N, 5.80. Found: C, 69.57; H, 4.69; N, 5.73.

C.  2-Phenyl-4H-pyrido[3,2-d]-1,3-dioxin-6-epoxyethane.

To a mixture of dimethyloxosulfonium methylide, prepared by refluxing a mixture of 132 mg. (13 m moles) of sodium hydride and 1.67 g. (13 m moles) of trimethylsulfonium chloride in 20 ml. of tetrahydrofuran (E. J. Corey, et al., J. Am. Chem. Soc., 87, 1353 [1965]), is added dropwise 2.4 g. (10 m moles) of 6-formyl-2-phenyl-4H-pyrido[3,2-d]-1,3-dioxin in 10 ml. of dry tetrahydrofuran while the mixture is maintained at 55° ± 2° C. Following the addition, which requires 1 hour, the mixture is stirred at 55° C. for an additional 1.5 hrs. The reaction mixture is concentrated in vacuo to 10 ml., 25 ml. of water added dropwise under nitrogen and the intermediate product extracted with ethyl acetate. The extract is separated, dried over magnesium sulfate and concentrated under reduced pressure to provide the product as an oily solid, 2.45 g.

NMR assay (CDCl$_3$): peaks — ppm ($\delta$): 3.1 (2H of epoxide); 4.0 (1H of epoxide); 5.19 (2H of 1,3-dioxin); 6.1 (1H of dioxin); 7.2 (C$_4$ and C$_5$ of pyridine) and 7.28 (5H of phenyl).

D.  6-(1-Hydroxy-2-t-butylaminoethyl)-2-phenyl-4H-pyrido[3,2-d]-1,3-dioxin.

To 2.3 g. (9 m moles) of 2-phenyl-4H-pyrido[3,2-d]-1,3-dioxin-6-epoxyethane in 25 ml. of ethanol is added .95 ml. of t-butylamine, and the resulting reaction mixture heated to the reflux temperature for 2 hrs. An additional 1 ml. of t-butylamine is added and the mixture maintained at 50° C. for 3 hrs. Solvent and excess amine are removed in vacuo to give 2.21 g. of the desired intermediate product.

E.  2-Hydroxymethyl-3-hydroxy-6-(1-hydroxy-2-t-butylaminoethyl)pyridine dihydrochloride.

One and five-tenths grams (4.8 m moles) of the above intermediate 6-(1-hydroxy-2-t-butylaminoethyl)-2-phenyl-4H-pyrido[3,2-d]-1,3-dioxin is dissolved in 20 ml. of acetone-water (1:1 v/v) and is treated with 1 ml. of 12N hydrochloric acid. After heating the solution to reflux for 5 hrs. the mixture is concentrated to an oil and dissolved in 100 ml. of ethanol. The water is azeotroped with 3 × 100 ml. portions of ethanol and the free base of the product generated by the addition of triethylamine. The solution is concentrated in vacuo to an oily slurry and the free base extracted from the triethylamine hydrochloride by extraction with acetone. The acetone extracts are combined, concentrated to an oil and the oil dissolved in 10 ml. of dry ethanol. Ethanol (0.184 ml.) containing hydrogen chloride (188 gm. HCl/ml. ethanol) is added and the solution added dropwise to 2 l. of dry isopropyl ether. The product is filtered and dried, 1.05 g. Further purification by recrystallization from methanol-acetone provides 950 mg. of the product which by infrared and nuclear magnetic resonance spectroscopy and thin-layer chromatography are identical to that in U.S. Pat. No. 3,700,681.

EXAMPLE 3

2-Hydroxymethyl-3-hydroxy-6-(1-hydroxy-2-t-butylaminoethyl)pyridine dihydrochloride A. 2,2-Dimethyl-6-hydroxymethyl-4H-pyrido[3,2-d]-1,3-dioxin To a 250 ml. flask, fitted with a condenser, drying tube, thermometer, and magnetic stirring bar is added 3.0 g. (19.3 m moles) of 2,6-bis(hydroxymethyl)-3-hydroxypyridine, 45 ml. (362 moles) of 2,2-dimethoxypropane, 60 ml. of dimethylformamide and 30 mg. of p-toluenesulfonic acid monohydrate, and the resulting reaction mixture heated to 110°–115° C. for 2.5 hrs. Sodium bicarbonate (500 mg.) is added and the yellow reaction mixture cooled to room temperature. The mixture is filtered, and the filtrate added to 100 ml. of water/100 ml. of ethyl acetate and allowed to stir for 20 min. The organic layer is separated, and the aqueous saturated with sodium chloride and extracted further with ethyl acetate. The combined ethyl acetate extracts are dried over magnesium sulfate and subsequently concentrated to a yellow oil, 3.47 g.

A 514 mg. sample of the residual oil in 15 ml. of ethanol/water (1:1) is treated with 1 ml. of a 5% acetic acid solution and allowed to stir for 3 hrs. The solution is made basic (pH 8) with a 5% sodium bicarbonate solution and most of the ethanol removed under reduced pressure. The residual is saturated with sodium chloride and extracted several times with methylene chloride. The combined, dried (MgSO$_4$) extracts are concentrated to dryness to provide the desired product, 332 mg., as a yellow oil.

NMR assay (CDCl$_3$): peaks — ppm ($\delta$): 1.5 (6H of 2 CH$_3$); 4.6 (2H of CH$_2$); 4.8 (2H — CH$_2$ of dioxin) and 7.0 and 7.25 (2H — C$_4$, C$_5$ of pyridine).

B. 2,2-Dimethyl-4H-pyrido[3,2-d]-1,3-dioxin-6-carboxaldehyde

A mixture of 4.55 g. (52.5 m moles) of activated manganese dioxide in 160 ml. of benzene contained in a flask fitted with a reflux condenser and Dean-stark distilling trap is heated under reflux until approximately 80 ml. of benzene has been removed through the trap. To the resulting suspension remaining in the flask is added 2.06 g. (10.5 m moles) of 2,2-dimethyl-6-hydroxymethyl-4H-pyrido[3,2-d]-1,3-dioxin in 20 ml. of benzene, and the refluxing continued for 3 hrs. The mixture is filtered and the filtrate is concentrated in vacuo to an oil which crystallizes, 1.85 g. The product is further purified by recrystallization from hexane, 1.3 g., m.p. 78.5°–79° C.

Anal. Calc'd for C$_{10}$H$_{11}$O$_3$N: C, 62.2; H, 5.7; N, 7.3. Found: C, 62.1; H, 5.8; N, 7.2.

NMR assay (CDCl$_3$): peaks — ppm ($\delta$): 1.6 (6H of 2 CH$_3$); 4.9 (2H — CH$_2$); 7.2 and 7.8 (2H — C$_4$, C$_5$ of pyridine); and 9.9 (1H — CHO).

C. 2,2-Dimethyl-4H-pyrido[3,2-d]-1,3-dioxin-6-epoxyethane

A 384 mg. sample of 50% sodium hydride in an oil suspension is washed free of the oil with pentane under a nitrogen atmosphere. To the oil free sodium hydride is added 10 ml. of dimethyl sulfoxide and the resulting suspension heated to 65°–70° C. for 45 min. The resulting gray solution is cooled to −5° to −8° C. and 20 ml. of tetrahydrofuran added. To this is then added 1.92 g. (9.5 m moles) of trimethylsulfonium iodide in 15 ml. of dimethyl sulfoxide, followed, after approximately one minute, by 1.3 g. (6.7 m moles) of 2,2-dimethyl-4H-pyrido[3,2-d]-dioxin-6-carboxaldehyde in 15 ml. of tetrahydrofuran. After 10 min. cooling is discontinued and the reaction mixture allowed to warm to room temperature. Water (30 ml.) and diethyl ether (40 ml.) are added, and the aqueous-dimethyl sulfoxide layer separated for further extractions with ether. The ether extracts are combined, dried over magnesium sulfate and concentrated to provide 1.11 g. of the product as a yellow oil.

Anal. Calc'd for C$_{11}$H$_{13}$O$_3$N: C, 63.8; H, 6.3; N, 6.8. Found: C, 63.2; H, 6.3; N, 6.6.

NMR assay (CDCl$_3$): peaks — ppm ($\delta$): 1.56 (6H of 2 CH$_3$); 3.03 (2H — epoxide); 3.9 (1H — epoxide); 4.87 (2H — CH$_2$); and 7.05 (2H — C$_4$, C$_5$ of pyridine).

D. 2,2-Dimethyl-6-(1-hydroxy-2-t-butylaminoethyl)-4H-pyrido[3,2-d]-1,3-dioxin

To 1.0 g. (4.8 m moles) of 2,2-dimethyl-4H-pyrido[3,2-d]-1,3-dioxin-6-epoxyethane is added 20 ml. of t-butylamine and the reaction mixture heated to reflux, t-butylamine being added periodically to replace any amount evaporated until a total of 80 ml. is used. After 90 hrs., heating is discontinued and the excess amine removed under reduced pressure. The product is isolated as a yellow solid, 1.168 g., m.p. 89.5°–92° C. The product is further purified by recrystallization from petroleum ether, m.p. 99°–100° C.

Anal. Calc'd for C$_{15}$H$_{24}$O$_3$N$_2$: C, 64.3; H, 8.6; N, 10.0. Found: C, 64.1; H, 8.5; N, 9.9.

NMR assay (CDCl$_3$): peaks — ppm ($\delta$): 1.1 (9H of C(CH$_3$)$_3$); 1.6 (6H of 2 CH$_3$); 3.13–2.46 (4H); 4.6 (1H); 4.83 (2H — CH$_2$ of dioxin); and 7.03 and 7.23 (2H — C$_4$, C$_5$ of pyridine).

E. 2-Hydroxymethyl-3-hydroxy-6-(1-hydroxy-2-t-butylaminoethyl)pyridine dihydrochloride To 10 ml. of methanol and 10 ml. of 10% hydrochloric acid is added 227 mg. of 2,2-dimethyl-6-(1-hydroxy-2-t-butylaminoethyl)-4H-pyrido[3,2-d]-1,3-dioxin, and the resulting reaction mixture allowed to stir at room temperature for 1.5 hrs. Removal of the solvents under vacuum at 70° C. provides 230 mg. of the desired product, which is identical by nuclear magnetic resonance spectroscopy to the product in U.S. Pat. No. 3,700,681.

EXAMPLE 4

Starting with benzophenone and acetophenone in place of benzaldehyde in the procedure of Example 2A-C there is prepared 2,2-diphenyl-4H-pyrido[3,2-d]-1,3-dioxin-6-epoxyethane and 2-methyl-2-phenyl-4H-pyrido[3,2-d]-1,3-dioxin-6-epoxyethane, respectively. Employing these as reagents in place of 2-phenyl-4H-pyrido[3,2-d]-1,3-dioxin-6-epoxyethane in the procedure of Example 2D-E, 2-hydroxymethyl-3-hydroxy-6-(1-hydroxy-2-t-butylaminoethyl)pyridine dihydrochloride, identical with that product from U.S. Pat. No. 3,700,681, is isolated.

EXAMPLE 5

2-Hydroxymethyl-3-benzyloxy-6-(1-hydroxy-2-t-butylaminoethyl)pyridine dihydrochloride Into a 500 ml. Parr bottle there are introduced 3.7 g. (0.01437 mole) of 2-hydroxymethyl-3-benzyloxypyridine-6-epoxyethane and 20 ml. t-butylamine under a nitrogen pressure of 30 p.s.i. and the mixture is shaken at 75° C. for 4.5 hrs. After cooling, the t-butylamine is removed under reduced pressure, the resulting oil is dissolved in 57 ml. of methanol and this solution is stirred as 13.0 ml. of 2.25 molar methanolic hydrogen chloride are slowly added. The temperature of the solution reaches 50° C. and the solution is cooled to 30° C. with an ice bath. Next there are added 70 ml. of diisopropyl ether. A slurry results and the slurry is stirred at room temperature for 30 min. prior to filtration. The recovered solid is washed with diisopropyl ether and is then dried under high vacuum overnight to obtain a yield of 3.99 g. (68.7%) of 2-hydroxymethyl-3-benzyloxy-6-(1-hydroxy-2-t-butylaminoethyl)pyridine dihydrochloride.

What is claimed is:

1. A process for producing a compound selected from the group consisting of

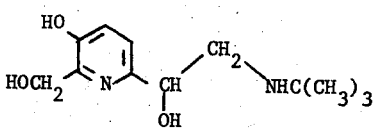

and the pharmaceutically accepted acid addition salts thereof, comprising the steps of heating 2-phenyl-4H-pyrido[3,2-d]-1,3-dioxin-6-epoxyethane with at least a molar amount of t-butylamine, and acid hydrolyzing the resulting product at a pH of from about 1 to 6.

2. The process of claim 1 wherein said pH is from 2 to 4.

3. The process of claim 1 wherein the heating step is carried out at 35° C. to reflux temperature.

4. The process of claim 1 wherein the heating setp is carried out in a closed system at reflux temperature at 85° C.

5. The process according to claim 2 wherein a mono- or diacid addition salt is formed by adding an acid selected from the group consisting of hydrochloric, hydrobromic, hydroiodic, nitric, sulfuric, sulfurous, phorphoric, acetic, lactic, citric, tartaric, succinic, maleic and gluconic acids to the product obtained by acid hydrolysis.

6. A process for producing a compound selected from the group consisting of

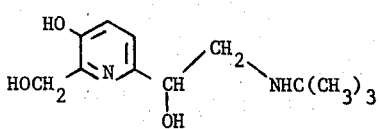

and the pharmaceutically accepted acid addition salts thereof, comprising the steps of heating a compound selected from the group consisting of

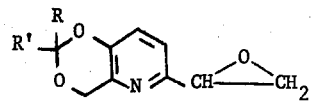

wherein R and R' are each selected from the group consisting of methyl and phenyl, with at least a molar amount of t-butylamine, and acid hydrolyzing the resulting product at a pH of from about 1 to 6.

7. The process of claim 6 wherein said pH is from 2 to 4.

8. The process of claim 6 wherein the heating step is carried out at 35° C. to reflux temperature.

9. The process of claim 6 wherein a mono- or diacid addition salt is formed by adding an acid selected from the group consisting of hydrobromic, hydroiodic, hydrochloric, nitric, sulfuric, sulfurous, phorphoric, acetic, lactic, citric, tartaric, succinic, maleic and gluconic acids to the product obtained by reaction with t-butylamine.

10. The process of claim 6 wherein R and R' are each methyl.

11. A compound selected from the group consisting of

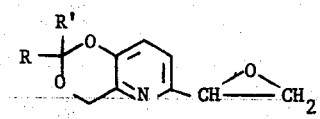

wherein R and R' are each selected from the group consisting of methyl and phenyl.

12. The compound of claim 11 of the formula

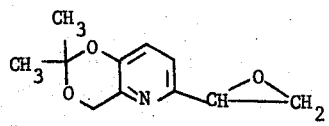

13. A compound of the formula

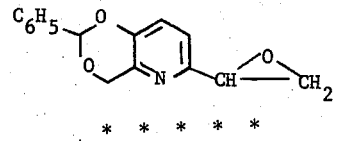

* * * * *